US010281469B2

(12) United States Patent
Tomiyama et al.

(10) Patent No.: US 10,281,469 B2
(45) Date of Patent: May 7, 2019

(54) MYCOPLASMA PNEUMONIAE DETECTION REAGENT AND APPLICATION OF SAME

(71) Applicant: TANAKA KIKINZOKU KOGYO K.K., Tokyo (JP)

(72) Inventors: Tetsuo Tomiyama, Tokyo (JP); Tsuyoshi Kenri, Tokyo (JP)

(73) Assignee: TANAKA KININZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/329,629

(22) PCT Filed: Jul. 27, 2015

(86) PCT No.: PCT/JP2015/071290
§ 371 (c)(1),
(2) Date: Jan. 27, 2017

(87) PCT Pub. No.: WO2016/017598
PCT Pub. Date: Feb. 4, 2016

(65) Prior Publication Data
US 2017/0242007 A1 Aug. 24, 2017

(30) Foreign Application Priority Data
Jul. 30, 2014 (JP) .................................. 2014-155388

(51) Int. Cl.
| C07K 16/00 | (2006.01) |
| G01N 33/569 | (2006.01) |
| C07K 16/12 | (2006.01) |
| C12N 5/10 | (2006.01) |
| C12N 15/02 | (2006.01) |
| G01N 33/577 | (2006.01) |
| G01N 33/558 | (2006.01) |

(52) U.S. Cl.
CPC ....... G01N 33/56933 (2013.01); C07K 16/12 (2013.01); C07K 16/1253 (2013.01); C12N 5/10 (2013.01); C12N 15/02 (2013.01); G01N 33/558 (2013.01); G01N 33/577 (2013.01); G01N 2333/30 (2013.01)

(58) Field of Classification Search
None
See application file for complete search history.

(56) References Cited

FOREIGN PATENT DOCUMENTS

| JP | S63-084484 | 4/1988 |
| JP | S63-184064 | 7/1988 |
| JP | 2012-006968 A | 1/2012 |
| JP | 2013-072663 A | 4/2013 |
| WO | WO 2009-072708 A1 | 11/2009 |
| WO | WO 2015/025968 A1 | 2/2015 |

OTHER PUBLICATIONS

WO, International Search Report for PCT/JP2015/071290, dated Oct. 13, 2015.
S. F. Dallo, et al. Biofunctional domains of the Mycoplasma pneumoniae P30 adhesin. Infection and Immunity, vol. 64, No. 7, Jul. 1996, pp. 2595-2601.
A. K. Varshney, et al. Cloning, Expression, and Immunological Characterization of the P30 Protein of Mycoplasma pneumoniae, Clinical and Vaccine Immunology, vol. 15, No. 2, Feb. 2008, pp. 215-220.
H.-Y. Chang, et al. Domain Analysis of Protein P30 in Mycoplasma pneumonia Cytadherence and Gliding Motility, Journal of Bacteriology, vol. 193, No. 7, Apr. 2011, pp. 1726-1733.
H.-Y. Chang, et al. Processing is Required for a Fully Functional Protein P30 in Mycoplasma pneumoniae Gliding and Cytadherence, Journal of Bacteriology, vol. 193, No. 20, Oct. 2011, pp. 5841-5846.
EP, Extended European Search Report dated May 26, 2017 in the corresponding European patent application 15826889.6.
Office Action for Taiwanese patent application No. 104124346, dated Oct. 5, 2018.
Official Communication for European patent application No. 15826889. 6, dated Dec. 18, 2018.

*Primary Examiner* — Jennifer E Graser
(74) *Attorney, Agent, or Firm* — Orrick, Herrington & Sutcliffe LLP; Joseph A. Calvaruso

(57) ABSTRACT

The purpose of the present invention is to provide a specific antibody applicable to immunochromatographic detection of *Mycoplasma pneumoniae* infections, and a detection reagent using the same, among others. Provided are a *Mycoplasma pneumoniae* detection reagent and kit that include a specific antibody against the P30 protein of *Mycoplasma pneumoniae*, and an immunochromatographic test device.

17 Claims, 1 Drawing Sheet
Specification includes a Sequence Listing.

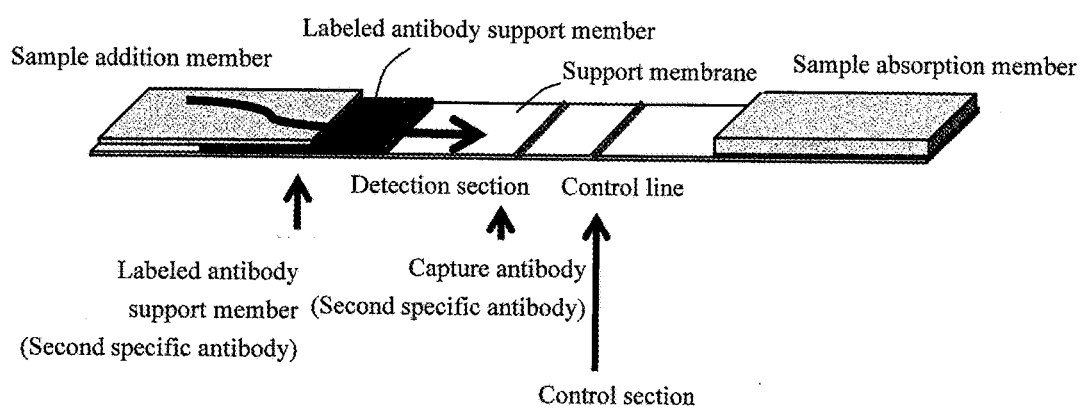

SEQUENCE LISTING

<160> NUMBER OF SEQ ID NOS: 4

<210> SEQ ID NO 1
<211> LENGTH: 274
<212> TYPE: PRT
<213> ORGANISM: Mycoplasma pneumoniae

<400> SEQUENCE: 1

```
Met Lys Leu Pro Pro Arg Arg Lys Leu Lys Leu Phe Leu Leu Ala Trp
1               5                   10                  15

Met Leu Val Leu Phe Ser Ala Leu Ile Val Leu Ala Thr Leu Ile Leu
            20                  25                  30

Val Gln His Asn Asn Thr Glu Leu Thr Glu Val Lys Ser Glu Leu Ser
        35                  40                  45

Pro Leu Asn Val Val Leu His Ala Glu Glu Asp Thr Val Gln Ile Gln
    50                  55                  60

Gly Lys Pro Ile Thr Glu Gln Ala Trp Phe Ile Pro Thr Val Ala Gly
65                  70                  75                  80

Cys Phe Gly Phe Ser Ala Leu Ala Ile Ile Leu Gly Leu Ala Ile Gly
                85                  90                  95

Leu Pro Ile Val Lys Arg Lys Glu Lys Arg Leu Leu Glu Glu Lys Glu
            100                 105                 110

Arg Gln Glu Gln Leu Ala Glu Gln Leu Gln Arg Ile Ser Ala Gln Gln
        115                 120                 125

Glu Glu Gln Gln Ala Leu Glu Gln Gln Ala Ala Ala Glu Ala His Ala
    130                 135                 140

Glu Ala Glu Val Glu Pro Ala Pro Gln Pro Val Pro Val Pro Pro Gln
145                 150                 155                 160

Pro Gln Val Gln Ile Asn Phe Gly Pro Arg Thr Gly Phe Pro Pro Gln
                165                 170                 175

Pro Gly Met Ala Pro Arg Pro Gly Met Pro Pro His Pro Gly Met Ala
            180                 185                 190

Pro Arg Pro Gly Phe Pro Pro Gln Pro Gly Met Ala Pro Arg Pro Gly
        195                 200                 205

Met Pro Pro His Pro Gly Met Ala Pro Arg Pro Gly Phe Pro Pro Gln
    210                 215                 220

Pro Gly Met Ala Pro Arg Pro Gly Met Pro Pro His Pro Gly Met Ala
225                 230                 235                 240

Pro Arg Pro Gly Phe Pro Pro Gln Pro Gly Met Ala Pro Arg Pro Gly
                245                 250                 255

Met Gln Pro Pro Arg Pro Gly Met Pro Pro Gln Pro Gly Phe Pro Pro
            260                 265                 270

Lys Arg
```

<210> SEQ ID NO 2
<211> LENGTH: 179
<212> TYPE: PRT
<213> ORGANISM: Mycoplasma pneumoniae

<400> SEQUENCE: 2

```
Gly Leu Pro Ile Val Lys Arg Lys Glu Lys Arg Leu Leu Glu Glu Lys
1               5                   10                  15
```

```
Glu Arg Gln Glu Gln Leu Ala Glu Gln Leu Gln Arg Ile Ser Ala Gln
            20                  25                  30

Gln Glu Gln Gln Ala Leu Glu Gln Gln Ala Ala Ala Glu Ala His
            35                  40                  45

Ala Glu Ala Glu Val Glu Pro Ala Pro Gln Pro Val Pro Val Pro Pro
 50                  55                  60

Gln Pro Gln Val Gln Ile Asn Phe Gly Pro Arg Thr Gly Phe Pro Pro
 65                  70                  75                  80

Gln Pro Gly Met Ala Pro Arg Pro Gly Met Pro Pro His Pro Gly Met
                85                  90                  95

Ala Pro Arg Pro Gly Phe Pro Pro Gln Pro Gly Met Ala Pro Arg Pro
            100                 105                 110

Gly Met Pro Pro His Pro Gly Met Ala Pro Arg Pro Gly Phe Pro Pro
            115                 120                 125

Gln Pro Gly Met Ala Pro Arg Pro Gly Met Pro Pro His Pro Gly Met
    130                 135                 140

Ala Pro Arg Pro Gly Phe Pro Pro Gln Pro Gly Met Ala Pro Arg Pro
145                 150                 155                 160

Gly Met Gln Pro Pro Arg Pro Gly Met Pro Pro Gln Pro Gly Phe Pro
            165                 170                 175

Pro Lys Arg

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
aggcatatgg gactgccaat tgtgaagcg                                29

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
caggtcgact tagcgttttg gtggaaaac                                29
```

MYCOPLASMA PNEUMONIAE DETECTION REAGENT AND APPLICATION OF SAME

TECHNICAL FIELD

The present invention relates to a *Mycoplasma pneumoniae* detection reagent, and to use thereof (an immunochromatographic test device, and a *Mycoplasma pneumoniae* infection testing method), among others. The present application claims priority to Japanese Patent Application Number 2014-155388 filed on Jul. 30, 2014, the entire contents of which are hereby incorporated by reference.

BACKGROUND ART

Aside from typical bacterial pneumonia, *Mycoplasma pneumoniae* is responsible for 30 to 40% of non-bacterial pneumonia that involves infiltrative shadows in chest radiography of lungs. *Mycoplasma pneumoniae* has been shown to be pathogenic among the species of *Mycoplasma* isolated from humans.

*Mycoplasma pneumonia* is common among infants and schoolchildren. The incubation period is 14 days, on average. The disease is reported to involve a wide range of complications, and in the case of children, complications such as encephalitis, Guillain-Barre syndrome and dermatitis (e.g., rashes) are developed in many cases. Though the rate of bacterial pneumonia has dramatically decreased over the last years, the percentage of *mycoplasma pneumonia* in all pneumonia cases has been increasing. *Mycoplasma pneumoniae* is the most common cause of community-acquired pneumonia after pneumococcus.

*Mycoplasma* is the smallest self-replicating microorganism, and cannot be easily observed with a light microscope. Unlike other bacteria, *Mycoplasma* lacks the cell wall, and does not respond to penicillin and the cephem antibiotics. The tetracycline antibiotics or macrolide antibiotics are commonly used for treatment.

Various methods described below are available for the diagnosis of *Mycoplasma pneumoniae* infections. The isolation culture method that uses a pharyngeal swab or sputum is used for a definitive diagnosis. However, the method requires a special medium and long days (2 to 4 weeks), and cannot be used for quick diagnosis. Another method detects antibodies produced in *Mycoplasma pneumoniae* infections. For example, serum antibodies are detected using methods such as particle agglutination (PA), and hemaggulutination reaction (IHA). However, neither of these techniques is applicable to diagnosis in the acute phase.

Determination by polymerase chain reaction (PCR) in a detection method based on the nucleic acid amplification of *Mycoplasma pneumoniae* in samples such as a pharyngeal swab and sputum has a strong correlation with results of the isolation culture method used to provide a definitive diagnosis. Use of LAMP (Loop-Mediated Isothermal Amplification) has also been reported as a tool simpler than PCR. However, these methods are not applicable to quick diagnosis because both PCR and LAMP involve complicated procedures, and require considerable labor for measurements.

*Mycoplasma pneumonia* effectively responds to only limited antibiotics, and there is a strong need at the clinic to determine the presence or absence of *Mycoplasma pneumoniae* infections at early stages of infection. As a rule, enzyme immunoassays (EIA) such as ELISA are applicable when specific antibodies are available. Antibodies are also applicable to various other assays such as chemiluminescence, and the dye and the fluorescence methods. However, all of these methods require dedicated measurement devices, and cannot be said as meeting the clinical needs. Immunochromatography is easy to operate, and enables a measurement in a short time period (for example, 10 to 20 min), without requiring special devices. However, it is not necessarily the case that the antibodies that are detectable by EIA are applicable to immunochromatography, and immunochromatography often requires more specific and sensitive antibodies. At present, anti-P1 protein monoclonal antibodies (PTL 1), and an immunochromatography reagent using anti-ribosomal protein L7/L12 protein-specific antibodies (PTL 2) are commercially available, and used for diagnosis of *Mycoplasma pneumoniae* infections. However, it cannot be said that these have high sensitivity, and that the performance is sufficient to meet the clinical needs.

CITED REFERENCES

Patent Literature

PTL 1: JP-A-2013-72663
PTL 2: JP-A-2012-6968

Non Patent Literature

NPL 1: Varshney A K et al., Clin Vaccine Immunol. February 2008; 15(2): 215-220.

DISCLOSURE OF THE INVENTION

Problems to be Solved by the Invention

The present invention is intended to provide a specific antibody applicable to immunochromatographic detection of *Mycoplasma pneumoniae* infections, and a detection reagent using same, among others.

Means for Solving the Problems

In our studies conducted to find a solution to the foregoing problems, the present inventors focused on the P30 protein as a possible target protein for more sensitive detection of *Mycoplasma pneumoniae* infections than that by the P1 protein. The P30 protein is a proline-rich (20.7%) adhesion protein with a molecular weight of 29,743. Previous studies have identified the P30 molecule, and antibodies against P30 are available. An ELISA assay using such antibodies is also reported (NPL 1). However, there is no report of the antibodies being used for immunochromatography. Our attempts to produce antibodies suited for immunochromatography successfully produced novel antibodies of superior performance. Immunochromatography using the antibodies enabled detection with clearly higher sensitivity than detection using antibodies against the P1 protein.

The invention below is based on this achievement.

[1] A *Mycoplasma pneumoniae* detection reagent comprising a specific antibody against the P30 protein of *Mycoplasma pneumoniae*.

[2] The detection reagent as described in [1], which is for immunochromatography.

[3] The detection reagent as described in [1] or [2], wherein the specific antibody is a monoclonal antibody.

[4] The detection reagent as described in [3], wherein the monoclonal antibody is an antibody produced by a hybridoma deposited with Deposition Number NITE BP-01880, or an antibody produced by a hybridoma deposited with Deposition Number NITE BP-01881.

[5] The detection reagent as described in any one of [1] to [4], wherein the specific antibody is an antibody prepared by using as an antigen a recombinant P30 protein lacking the first 95 amino acids from the N-terminus of the P30 protein.

[6] The detection reagent as described in [5], wherein the recombinant P30 protein consists of the amino acid sequence of SEQ ID NO: 2.

[7] The detection reagent as described in any one of [1] to [6], wherein the specific antibody is labeled with a colored synthetic polymer particle or with a metal colloid particle.

[8] The detection reagent as described in [7], wherein the metal colloid particle is a gold colloid particle.

[9] A *Mycoplasma pneumoniae* detection kit comprising the detection reagent of any one of [1] to [8].

[10] An immunochromatographic test device comprising:
a first specific antibody against the P30 protein of *Mycoplasma pneumoniae*, a second specific antibody against the P30 protein of *Mycoplasma pneumoniae*, and a support membrane,
wherein the first specific antibody is immobilized on the support membrane to constitute a detection section, and
wherein the second specific antibody is labeled with a labeling substance, and is supported at a distance from the detection section.

[11] The test device as described in [10],
wherein the first specific antibody is an antibody produced by a hybridoma deposited with Deposition Number NITE BP-01881, and
wherein the second specific antibody is an antibody produced by a hybridoma deposited with Deposition Number NITE BP-01880.

[12] The test device as described in [10] or [11], wherein the labeling substance is a colored synthetic polymer particle or a metal colloid particle.

[13] The test device as described in [12], wherein the metal colloid particle is a gold colloid particle.

[14] A *Mycoplasma pneumoniae* infection testing method using the immunochromatographic test device of any one of [10] to [13].

[15] The testing method as described in [14], which uses a biological material as a sample.

[16] The testing method as described in [15], wherein the biological material is a pharyngeal swab or a nasal aspirate.

[17] A monoclonal antibody specific to the P30 protein of *Mycoplasma pneumoniae*, and produced by a hybridoma deposited with Deposition Number NITE BP-01880 or NITE BP-01881.

[18] A labeled antibody comprising the specific monoclonal antibody of [17] labeled with a metal colloid particle.

[19] The labeled antibody as described in [18], wherein the metal colloid particle is a gold colloid particle.

[20] A hybridoma deposited with Deposition Number NITE BP-01880 or NITE BP-01881.

BRIEF DESCRIPTION OF DRAWINGS

FIG. 1 shows an exemplary configuration of a test strip.

EMBODIMENTS FOR CARRYING OUT THE INVENTION

The present invention provides a reagent (*Mycoplasma pneumoniae* detection reagent) and a kit useful for the detection of *Mycoplasma pneumoniae*. A feature of the *Mycoplasma pneumoniae* detection reagent of the present invention is that the reagent is also applicable to immunochromatography. (This does not exclude the reagent's applicability to other techniques such as EIA, and western blotting.) Specifically, the reagent of the present invention enables highly sensitive immunochromatographic detection of *Mycoplasma pneumoniae* infections. The kit of the present invention includes the reagent of the present invention as a main constituting element. The kit may include other reagents (e.g., a developing solvent, and a buffer), and/or devices or instruments (e.g., a container, and a reaction apparatus) used in the detection method. The kit also may include antigens (the P30 protein, or a part of the protein). The kit of the present invention typically comes with an instruction manual.

The reagent of the present invention contains a specific antibody against the P30 protein of *Mycoplasma pneumoniae* as an active ingredient. The antibody constituting the reagent of the present invention may be a polyclonal antibody or a monoclonal antibody. A monoclonal antibody is preferred for sensitivity.

The specific polyclonal antibody against the P30 protein can be produced according to an ordinary method. For example, the P30 protein is subcutaneously or intraperitoneally administered to a suitable mammal (for example, a mouse, a rat, or a rabbit) after mixing the protein with a suitable adjuvant as required. A high-titer anti-serum can be obtained by boosting immunity after 2 to 3 weeks from initial immunization using an ordinary method. As an example, blood is collected after 1 week from final immunization, and the serum is separated. An immunoglobulin fraction is then obtained by the same method as common antibody purification methods such as ammonium sulfate precipitation and ion chromatography.

The P30 protein monoclonal antibody can be obtained from a hybridoma produced according to an ordinary method, using the information of this specification as a reference. For example, a suitable mammal (for example, a mouse or a rat) is immunized with the P30 protein after mixing the protein with a suitable adjuvant as required. An antibody producing cell, such as a spleen cell and a B lymphocyte from the animal is then fused with a myeloma cell derived from a suitable animal (for example, a mouse or a rat) to obtain a hybridoma. Cell fusion may be effected by using techniques such as the polyethylene glycol (PEG) method, in which the antibody producing cell and the myeloma cell are fused to each other in the presence of polyethylene glycol and the like in a suitable medium. After the cells have fused, the cells are screened for a hybridoma with a selection medium such as HAT medium (a medium containing hypoxanthine, aminopterin, and thymidine), and the hybridoma is screened for the ability to produce an antibody that recognizes the P30 protein, using an ordinary method (for example, EIA). The hybridoma producing the desired antibody is then cloned by an ordinary method (for example, a limiting dilution method), and the clones are screened for a hybridoma producing a monoclonal antibody.

The P30 protein (antigen) used for immunization in antibody production can be mass produced by genetic recombination using *Escherichia coli*. P30, a protein composed of 274 amino acids, has two hydrophobic transmembrane domains within the sequence of the first 95 amino acids from the N-terminus. Production of P30 protein in full length with *Escherichia coli* involves difficulties in lysing the cells, and makes it difficult to handle the cells. To circumvent this, a recombinant P30 protein lacking preferably the first 95 amino acids of the P30 protein is prepared through expression (the amino acid sequence of the recombinant P30 protein is represented by SEQ ID NO: 2), and used as antigen protein.

The present inventors successfully produced a plurality of monoclonal antibodies that specifically recognizes the P30 protein, as will be described in the Examples below. These antibodies were identified by designating clone numbers #1 to #19. Among these antibodies, hybridoma clone #3 and hybridoma clone #9 produced antibody #3 and antibody #9, respectively, that showed high immunochromatographic sensitivity. These clones have been deposited at the predetermined depositary, as follows.

Hybridoma Clone #3
Depository: The National Institute of Technology and Evaluation, International Patent Organism Depositary; 122, 2-5-8, Kazusa-Kamatari, Kisarazu, Chiba, Japan, 292-0818.
Deposition Date: Jun. 23, 2014
Deposition Number: NITE BP-01880

Hybridoma Clone #9
Depository: The National Institute of Technology and Evaluation, International Patent Organism Depositary; 122, 2-5-8, Kazusa-Kamatari, Kisarazu, Chiba, Japan, 292-0818.
Deposition Date: Jun. 23, 2014
Deposition Number: NITE BP-01881

The anti-P30 protein antibody (polyclonal antibody or monoclonal antibody) is labeled, as required. Labeling may be performed by using an ordinary method. The labeling substance used for labeling is favorably an insoluble particulate substance. Examples of the insoluble particulate substance include: colored synthetic polymer particles obtained by dye-molecule labeling of synthetic polymers such as latex, polyethylene, polypropylene, polystyrene, a styrene-butadiene copolymer, polyvinyl chloride, polyvinyl acetate, polyacrylamide, polymethacrylate, a styrene-methacrylate copolymer, polyglycidyl methacrylate, and an acrolein-ethylene glycol dimethacrylate copolymer; metal colloid particles (gold, silver, copper, iron, platinum, palladium, and a mixture thereof (for example, a mixture of gold and platinum, a mixture of gold and silver, and a mixture of palladium and platinum)); and red blood cells. Preferably, the particles are ones that allow changes to be easily and quickly checked by visual inspection, and colored synthetic polymer particles or metal colloid particles may be used to this end. The particles have a particle size of, for example, 15 to 100 nm, preferably 30 to 80 nm. The metal colloid particles may be commercially available products, or may be prepared by using an ordinary method. For reasons such as usability, the metal colloid particles are preferably gold colloid particles.

In the case of labeling by metal colloid particles, 0.1 to 100 mg, preferably 0.5 to 20 mg of anti-P30 protein antibody is typically added to 1 L of a metal colloid particle solution (typically, an absorbance of about 2.0 at 540 nm), and the mixture is refrigerated, or stirred at room temperature for 5 minutes to 24 hours. After blocking with bovine serum albumin (BSA; typically 0.01 to 10 g, preferably 0.1 to 2 g) and the like, the solution is centrifuged, and the resulting precipitate is obtained as anti-P30 protein antibodies labeled with the metal colloid particles. The buffer may be one commonly used for immunoassay, for example, such as Tris buffer, and phosphate buffer. The buffer has a pH of typically 4.5 to 9.5, preferably 5.5 to 8.5.

A test instrument (immunochromatographic test device) for detecting *Mycoplasma pneumoniae* infection may be constructed using the anti-P30 protein antibody. Specifically, the present invention also provides an immunochromatographic test device using the anti-P30 protein antibody.

The device of the present invention includes a first specific antibody (first anti-P30 protein antibody) against the P30 protein of *Mycoplasma pneumoniae*, a second specific antibody (second anti-P30 protein antibody) against the P30 protein of *Mycoplasma pneumoniae*, and a support membrane.

The first anti-P30 protein antibody is immobilized on the support membrane to constitute a detection section. The second specific antibody is labeled with a labeling substance, and is supported at a distance from the detection section.

As used herein, "immobilize" means disposing the antibody on a support such as a membrane so that the antibody is immovable. The term "support" as used herein means that the antibody is disposed so as to be movable within the support or on the support surface. The following describes the configuration of the test device, with reference to FIG. 1 (a test strip as a specific example). The first specific antibody and the second specific antibody are both specific to the P30 protein. Preferably, the first specific antibody and the second specific antibody are antibodies having different specificity to the P30 protein, for example, different anti-P30 protein antibodies. The first specific antibody is a capture antibody, and constitutes a detection section by being immobilized on the support. As used herein, "detection section" refers to a site where the presence of an antigen is detected by capturing the conjugate of the sample antigen and the first specific antibody formed by antigen-antibody reaction.

The support uses a material that can bind protein through physical actions such as electrostatic action and hydrophobic interaction, and on which substances such as sample components, the antigen-first specific antibody conjugate, and the control labeled substance can develop. Examples of support membrane materials include nitrocellulose, polyvinylidene difluoride (PVDF), and cellulose acetate. Preferably, the support has a form of a membrane (support membrane). It is preferable that the support also include a control section for checking whether the sample has appropriately developed, in addition to the detection section. A substance that can bind to a control standard substance is immobilized on the control section. Preferably, the detection section and the control section are disposed on the support in the form of lines across the direction of development (the lines are also referred to as "test line" and "control line", respectively). The locations of the detection section and the control section on the support are not particularly limited. Typically, the control section is formed downstream of the detection section.

The capture antibody, and the substance that can bind to the control labeled substance may be immobilized according to an ordinary method as may be decided according to the type of support. For example, a suitable dilution of an antibody solution is applied using a commercially available antibody coater, and dried. Immobilization is thus achieved. The capture antibody is immobilized at the detection site in an amount of preferably 0.05 to 10 µg, more preferably 0.1 to 3 µg.

The second specific antibody is a labeled antibody, labeled with a labeling substance. The second specific antibody is supported on a support, such as a membrane, at a distance from the detection site. Typically, the support supporting the labeled antibody is different from the support on which the capture antibody is immobilized. It is, however, possible to support the labeled antibody on the same support used to immobilize the capture antibody. The labeled antibody support member supporting the second specific antibody (labeled antibody) is disposed upstream of the detection section. The labeled antibody support member supports the labeled antibody in a dry state, and releases the labeled antibody upon being impregnated with liquid. Examples of the material of the labeled antibody support member include a glass fiber, a cellulose fiber, and a plastic fiber. The labeled antibody can be supported on the labeled antibody support member by impregnating the labeled antibody support member with a suitable buffer containing the labeled antibody, or by adding a suitable buffer containing the labeled antibody to the labeled antibody support member, followed by drying. The labeled antibody is supported on the labeled antibody support member in an amount of preferably 0.01 to 1 µg, more preferably 0.03 to 0.3 µg.

A sample addition member is disposed on the upstream side of the labeled antibody support member. Preferably, at least the lower surface of a downstream region of the sample addition member is in contact with the top surface of an upstream region of the labeled antibody support member. Preferably, a portion of the labeled antibody support member lies between the lower surface of the sample addition member and the top surface of an upstream region of the support. Preferably, an absorption member is provided on the downstream side of the support. The absorption member is disposed so that the lower surface of an upstream region of the absorption member is in contact with the top surface of a region downstream of the detection section of the support.

In the test device of the present invention, a liquid sample dropped onto the sample addition member after an optionally performed pretreatment infiltrates into the labeled antibody support member, and the mixture of the sample and the labeled antibody migrates to the support (typically, the support membrane), and develops toward the detection site in the support. The antigen and the labeled antibody forms an immunocomplex when the sample contains the P30 protein (antigen; in the case of a *Mycoplasma pneumoniae* infection). At the detection section, the capture antibody captures the complex through an antigen-antibody reaction, and the conjugate accumulates and develops color. The presence or absence of antigen in the sample can then be determined by visually checking the extent of the color at the detection section. When the support has the control section, the control labeled substance released from the labeled antibody support member is captured by the substance that can bind to the control labeled substance at the control section, and the conjugate accumulates and develops color. When the labeled antibody is used also as a control labeled substance, the residual labeled antibody that did not form a conjugate with the antigen in the sample passes through the detection site, and is captured by the substance that is immobilized at the downstream control section to bind the labeled antibody. The conjugate accumulates and develops color.

The sample used in the test device of the present invention is a sample potentially containing *Mycoplasma pneumoniae*. Examples of biological materials that may be used as samples may include a pharyngeal swab, a nasal swab, a nasal aspirate, a nasal wash, sputum and an alveolar wash, but are not limited thereto.

As a sample pretreatment, a biological sample collected from a subject with a potential *Mycoplasma pneumoniae* infection may be dissolved in a pretreatment reagent to prepare a liquid to be dropped onto the test device. Such a pretreatment is performed to enable sample development, or to desirably develop the sample. Various buffers may be used for the pretreatment reagent. The buffer may be one commonly used for immunoassays, for example, such as Tris buffer, phosphate buffer, and Good buffer. The pretreatment reagent may contain a surfactant to inhibit non-specific binding reaction. The surfactant may be, for example, Triton X-100 (polyethylene glycol mono-p-isooctyl phenyl ether), Tween 20 (polyoxyethylene sorbitan monolaurate), Tween 80 (polyoxyethylene sorbitan monooleate), CHAPS (3-[(3-cholamidopropyl)dimethylammonio]propanesulfonate), or SDS (sodium dodecyl sulfate). Two or more surfactants may be used in combination.

The present invention is described below in more detail using Examples. The present invention, however, is not limited to the Examples below.

EXAMPLES

1. Production of Monoclonal Antibodies Specific to *Mycoplasma pneumoniae* P30 Protein
1-1. Preparation of Antigen Protein The P30 protein (SEQ ID NO: 1) has two hydrophobic transmembrane domains within the sequence of the first 95 amino acids from the N-terminus. A recombinant P30 protein (the amino acid sequence is represented by SEQ ID NO: 2) lacking the first 95 amino acids from the N-terminus of the P30 protein was expressed in *Escherichia coli*, and used as an antigen protein. Briefly, the antigen protein was prepared according to the following procedures. First, a P30 gene fragment is amplified by PCR, using the genomic DNA of the *Mycoplasma pneumoniae* (*M. Pneumoniae*) M129 strain as a template. The PCR primers have the following sequences: AGG CATATGGGACTGCCAATTGTGAAGCG (SEQ ID NO: 3), and CAGGTCGACTTAGCGTTTTGGTGGAAAAC (SEQ ID NO: 4) (the underscores in these sequences are cutting sites by restriction enzymes NdeI and SalI, respectively). The amplified P30 gene fragment is incorporated at the NdeI-SalI site of a pCold ProS2 expression vector available from Takara Bio, and the resulting vector is used as a recombinant P30 expression vector. The P30 expression vector is introduced into the *Escherichia coli* BL21 strain, and the recombinant P30 protein is expressed by low-temperature culture at 15° C. with addition of 1 mM isopropyl-β-D-thiogalactopyranoside (IPTG). The recombinant P30 protein expressed in *Escherichia coli* is purified using a his-tag purification column and gel filtration. The purified recombinant P30 protein is quantified, and a suitable amount is used as an immunizing antigen.

1-2. Immunization, and Antibody Purification

Experiments were conducted to obtain specific monoclonal antibodies against the antigen protein, as follows.
Materials
(1) Antigen
  Recombinant P30 purified protein
(2) Animal immunized
  Three BALB/cA female mice, 6 weeks of age (CLEA Japan)
(3) Adjuvant
  TiterMax Gold (G-3; Funakoshi Corporation)
(4) Mouse Myeloma Cell
  P3U1
(5) Medium, Equipment, Reagents
  RPMI-1640 medium (11875-119 GIBCO)
  Sodium pyruvate solution (11360-070 GIBCO)
  Penicillin-streptomycin-glutamine solution (10378-016 GIBCO)
  HAT supplement (21060-017 GIBCO)
  HT supplement (11067-030 GIBCO)
  FBS (S1560 BWT)

PEG 1500 (783641 Roche)
DMSO (D2650 SIGMA)
96-Well culture plate (92696 TPP)
24-Well culture plate (92424 TPP)
Sterilized petri dish (34153 Nipro)
Cryogenic tube (MS-4503 Sumitomo Bakelite)
(6) Antibody screening equipment, Reagents
ELISA microplate (442404 nunc)
Anti-mouse IgG-labeled antibody (1030-04 Cosmo Bio)
Monoclonal antibody isotyping kit (1493027 Roche)
(7) Mouse ascites production, antibody purification
BALB/cA, female, retired (CLEA Japan)
Pristane (42-002 Cosmo Bio)
HiTrap Protein G (17-0404-03 GE Healthcare)
Methods
(1) Immune Sensitization of Mouse The P30 protein was adjusted to 1.6 mg/ml, and mixed with the same amount of TiterMax Gold, and an emulsion was prepared using a glass syringe. The emulsion was subcutaneously administered to the BALB/cA mouse in an antigen amount of 100 µg in two separate portions in a 2-week interval. After 1 to 2 weeks, 40 µg of a P30 antigen solution was subcutaneously administered alone. After 3 days, whole blood was collected under anesthesia, and the spleen and lymph nodes were removed.
(2) Myeloma Cell Culture Mouse myeloma cells (P3U1) were subcultured on a medium (RPMI medium) that had been prepared by adding pyruvic acid, glutamic acid, and penicillin-streptomycin to RPMI1640 medium. The medium was used after adding 10% FBS. For cell fusion, cells with a stable logarithmic growth phase were used.
(3) Cell Fusion The lymph tissues collected from the sensitized mouse were each sliced on a #200 mesh, and the lymphocytes were collected through filtration by adding a medium to the slice being gently held with a glass rod fitted with a silicon stopper. The cells were washed by centrifugation performed at 1,200 rpm for 10 min, and the number of cells was counted. The myeloma cells were transferred to a 50-ml conical tube, counted, and washed by centrifugation at 1,000 rpm for 5 min. After that, the cell number was adjusted to make the lymphocyte:myeloma cell ratio 5:1 to 10:1, and the cells were mixed and centrifuged (1,200 rpm, 10 min) to obtain a cell pellet.

For cell fusion, a 1-mL PEG solution was added to the cell pellet while gently stirring the mixture over the course of 1 min, and a reaction was allowed by stirring the mixture for 2 min. The same procedure was repeated three times after adding 1 ml of an RPMI 1640 solution over the course of 1 min, and 12 ml of an RPMI 1640 solution was added over the course of 3 min. The mixture was placed in a 37° C. incubator for 10 min, and the cells were harvested by performing centrifugation at 1,000 rpm for 5 min. The collected cells were suspended in an RPMI medium containing 15% FBS with a HAT supplement, and inoculated on ten 96-well culture plates. Mouse thymocytes were used as feeder cells.

The cells were cultured in a $CO_2$ incubator for 1 week to allow selective hybridoma growth.
(4) Antibody Screening The P30 protein (50 µl) diluted to 1 µg/ml with PBS was applied to an ELISA 96-well microplate, and reaction was allowed either at room temperature for 2 h, or overnight under refrigerated conditions.

After 1 week from cell fusion, an about 50 µl of culture supernatant was aseptically collected from each culture plate, and applied to the antigen-coated plate. Reaction was allowed at room temperature for 1 h. After washing the plate three times with physiological saline, an enzyme labeled anti-mouse IgG antibody that had been diluted 2,500 times with 0.5% skim milk was reacted at room temperature for 1 h. After washing the plate using the same procedure, a color was developed with an enzyme substrate solution, and antigen-binding monoclonal antibody-positive wells were selected.
(5) Cloning The hybridoma selected by ELISA was cloned using the limiting dilution method. Specifically, a cell suspension was prepared, and inoculated to a 96-well culture plate that had been inoculated with the feeder cells. The cell suspension was inoculated so that the plate contained a single hybridoma cell per well. The plate was checked for colony growth after 1 week, and antibody screening was performed in the same manner. Cloning was performed twice to confirm that the clones were complete single cells. An RPMI medium supplemented with 15% FBS and a HT supplement was used as medium.
(6) Establishment of Clones, and Cell Freezing The single-cell hybridomas were expanded from a 24-well culture plate to a petri dish, and cryopreserved in 2 to $5 \times 10^8$ cells/tube. The cryopreservation used a medium that had been prepared by adding 10% DMSO to an RPMI medium supplemented with 15% FBS and HT supplement, and the cells were preserved in a −85° C. ultralow temperature freezer by being wrapped in a paper towel.
(7) Subclass Measurement Subclass measurement was conducted for a sufficiently cloned culture supernatant, using a commercially available immunochromatography technique according to the manual.
(8) Mouse Ascites Production, Antibody Purification The hybridoma cells (0.5 to $1 \times 10^7$) were inoculated to the abdominal cavity of a BALB/cA retired mouse that had been intraperitoneally administered with 0.5 ml of pristane at least one week in advance, and the retained ascites fluid was obtained after about 7 to 10 days. The ascites fluid was sufficiently coagulated, and centrifuged at 3,000 rpm for 15 min to precipitate a solid. After separating the supernatant, 0.1% sodium azide was added as an antiseptic to the supernatant, and the liquid was preserved under refrigerated conditions until purification.

Antibody purification from the ascites fluid was performed with a HiTrap Protein G column. PBS was used for binding and washing of antibodies to and from the protein G column. A 0.1 M glycine-hydrochloric acid buffer (pH 2.8) was used for the elution of antibodies after washing. 1M Tris was used to neutralize the eluted IgG. The eluted antibodies were concentrated with 50% saturated ammonium sulfate, and thoroughly dialyzed to PBS. The antibodies were preserved under refrigerated conditions after adding 0.05% sodium azide.

A purification assay of the purified antibodies was conducted by cellulose acetate membrane electrophoresis, and purification was confirmed by the appearance of a single band in the γ region.
Results Cell fusion experiment was conducted using three mice. As a result, primary screening selected 14 clones from mouse No. 1, 1 clone from mouse No. 2, and 14 clones from mouse No. 3. A total of 19 clones were further cloned after examining non-specific reaction and colony growth, and monoclonal antibody-producing hybridomas were established (clones #1 to #19). The established hybridomas were then used to produce mouse ascites, and 2 to 7 ml of ascites fluid was obtained. The ascites fluid thus obtained was checked for antibody content using cellulose acetate membrane electrophoresis, and the antibodies were purified to IgG with HiTrap Protein G. The purified antibodies from each clone were evaluated by immunochromatography. Of the 19 clones, desirable results were obtained in a combination of clone #3 and clone #9, and the antibodies were usable for the assay system. The subclass was IgG1κ in both clone #3 and clone #9. The hybridoma clones #3 and #9 have been deposited, as follows.

Hybridoma Clone #3
Depository: The National Institute of Technology and Evaluation, International Patent Organism Depositary; 122, 2-5-8, Kazusa-Kamatari, Kisarazu, Chiba, Japan, 292-0818.
Deposition Date: Jun. 23, 2014
Deposition Number: NITE BP-01880

Hybridoma Clone #9
Depository: The National Institute of Technology and Evaluation, International Patent Organism Depositary; 122, 2-5-8, Kazusa-Kamatari, Kisarazu, Chiba, Japan, 292-0818.
Deposition Date: Jun. 23, 2014
Deposition Number: NITE BP-01881

2. Production of Immunochromatography Test Device 2-1. Preparation of Labeled Antibody Support Member Considering the foregoing results, the anti-P30 monoclonal antibody (P30-3) produced by hybridoma clone #3 was used as labeled antibody. The anti-P30 monoclonal antibody (P30-3) was diluted with 5 mM phosphate buffer (pH 7.4) in a concentration of 0.05 mg/ml. After adding and mixing 0.1 ml of 50 mM phosphate buffer (pH 7.4) to 0.5 ml of a gold colloid suspension (BBI: average particle 60 nm), 0.1 ml of the diluted anti-P30 monoclonal antibody solution was added, and the mixture was allowed to stand at room temperature for 10 min. To this solution after standing was then added 0.1 ml of a 10 mass % bovine serum albumin (BSA) solution diluted with 10 mM phosphate buffer. The mixture was thoroughly stirred, and centrifuged at 8,000× g for 15 min. After removing the supernatant, 10 mM phosphate buffer (pH 7.4) was added to the residue again, and the mixture was thoroughly dispersed with an ultrasonic homogenizer to produce a labeled antibody solution. The labeled antibody solution was uniformly added to a glass fiber pad (Millipore: GFCP203000) measuring 16 mm in width and 100 mm in length, and dried with a vacuum dryer to obtain the labeled antibody support member.

2-2. Preparation of Nitrocellulose Support Membrane having Detection Section and Control Section The anti-P30 monoclonal antibody (monoclonal antibody P30-9 produced by hybridoma clone #9) different from the labeled antibody used in Section 2-1 above was diluted in a concentration of 1.3 mg/ml with phosphate buffer (pH 7.4) containing 5 mass % of isopropyl alcohol to prepare an antibody (capture antibody) solution to be immobilized at the detection section. The antibody solution to be immobilized at the detection section was applied to a nitrocellulose membrane (Millipore: HF120; 25 cm in length, 2.5 cm in width) at a distance of 1 cm from one end along the long axis of the membrane (this end is the upstream end of the direction of development, and the opposite end is the downstream end). Here, the antibody solution was applied in the form of a line in an amount of 1 μl/cm, using an antibody coater (BioDot). The anti-mouse IgG antibody was also applied in the form of a line to the nitrocellulose membrane at a distance of 1.5 cm from the upstream end, in an amount of 1 mg/ml. After being coated, the antibodies were dried at 42° C. for 60 min to obtain a nitrocellulose support membrane having a detection section and a control section.

2-3. Production of Immunochromatography Test Device

A plastic backing sheet was attached to the surface (lower surface) of the nitrocellulose support membrane produced in Section 2-2 above, opposite the antibody-coated surface (top surface). The labeled antibody support member of Section 2-1 above was then attached over the top surface of the nitrocellulose support membrane in a distance of 2 mm at the upstream end of the nitrocellulose membrane. Separately, a glass fiber sample pad (available from Pall Corporation; 8000006801) measuring 5 mm in width and 23 mm in length was attached over the top surface of the labeled antibody support member in a distance of 2 mm. An absorption pad (available from Pall Corporation) measuring 5 mm in width and 25 mm in length was also attached over the top surface of the nitrocellulose support membrane in a distance of 15 mm at the downstream end of the nitrocellulose support membrane. Finally, the device was cut along the long axis at 5 mm intervals to obtain individual immunochromatography test devices.

3. Comparison of *Mycoplasma pneumoniae* Detection Sensitivity

The *Mycoplasma pneumoniae* FH strain (ATCC) was cultured in Chanock medium at 37° C. for 7 days. By using the culture liquid as a sample, the anti-P30 monoclonal antibodies (using the above immunochromatography test device) and anti-P1 monoclonal antibodies were compared to each other for their immunochromatographic sensitivity. Monoclonal antibodies used are as follows. The test device used for the latter method was produced according to the method described above, using anti-P1 monoclonal antibodies (P1-4 and P1-115: Toyama Research Laboratory).

P30 Immunochromatography
Labeled antibody (for gold colloid sensitization): P30-3
Capture antibody (for membrane sensitization): P30-9

P1 Immunochromatography
Labeled antibody (for gold colloid sensitization): P1-4
Capture antibody (for membrane sensitization): P1-115

The results of experiment are presented in the table below.

TABLE 1

| Culture dilution factor | P30 immunochromatography | P1 immunochromatography |
|---|---|---|
| 1:100 | +++ | + |
| 1:200 | +++ | − |
| 1:400 | ++ | − |
| 1:800 | + | − |
| 1:1600 | − | − |
| Control (medium) | − | − |

As shown in the table, the detection sensitivity of the immunochromatography using the anti-P30 monoclonal antibodies was far superior to the detection sensitivity of the immunochromatography using the anti-P1 monoclonal antibodies.

As demonstrated above, anti-P30 monoclonal antibodies of excellent characteristics were successfully produced, which enabled immunochromatographic detection of *Mycoplasma pneumoniae* with much higher sensitivity than achievable by the existing method.

INDUSTRIAL APPLICABILITY

The present invention provides anti-P30 monoclonal antibodies applicable to immunochromatography. Immunochromatography using the monoclonal antibodies enables easy, quick, and high-sensitive detection of *Mycoplasma pneumoniae* infections.

This invention is in no way limited by the descriptions of the embodiments and Examples above. Various modified embodiments easily achieved by a skilled person without departing from the descriptions of the scope of the claims are encompassed in the present invention. The contents of the publications, including the research papers, patent applications, and patent publications described in this specification are hereby incorporated by reference in its entirety.

The invention claimed is:

1. A *Mycoplasma pneumoniae* detection reagent comprising a specific antibody against the P30 protein of *Mycoplasma pneumoniae*, wherein the specific antibody is a monoclonal antibody produced by a hybridoma deposited with Deposition Number NITE BP-01880, or a monoclonal antibody produced by a hybridoma deposited with Deposition Number NITE BP-01881.

2. The detection reagent according to claim 1, which is for immunochromatography.

3. The detection reagent according to claim 1, wherein the specific antibody is an antibody prepared by using as an antigen a recombinant P30 protein lacking the first 95 amino acids from the N-terminus of the P30 protein.

4. The detection reagent according to claim 3, wherein the recombinant P30 protein consists of the amino acid sequence of SEQ ID NO: 2.

5. The detection reagent according to claim 1, wherein the specific antibody is labeled with a colored synthetic polymer particle or with a metal colloid particle.

6. The detection reagent according to claim 5, wherein the metal colloid particle is a gold colloid particle.

7. A *Mycoplasma pneumoniae* detection kit comprising the detection reagent of claim 1.

8. An immunochromatographic test device comprising:
a first specific antibody against the P30 protein of *Mycoplasma pneumoniae*, wherein the first specific antibody is a monoclonal antibody produced by a hybridoma deposited with Deposition Number NITE BP-01881,
a second specific antibody against the P30 protein of *Mycoplasma pneumoniae*, and a support membrane, wherein the second specific antibody is a monoclonal antibody produced by a hybridoma deposited with Deposition Number NITE BP-01880, wherein the first specific antibody is immobilized on the support membrane to constitute a detection section, and
wherein the second specific antibody is labeled with a labeling substance, and is supported at a distance from the detection section.

9. The test device according to claim 8, wherein the labeling substance is a colored synthetic polymer particle or a metal colloid particle.

10. The test device according to claim 9, wherein the metal colloid particle is a gold colloid particle.

11. A *Mycoplasma pneumoniae* infection testing method using the immunochromatographic test device of claim 8.

12. The testing method according to claim 11, which uses a biological material as a sample.

13. The testing method according to claim 12, wherein the biological material is a pharyngeal swab or a nasal aspirate.

14. A monoclonal antibody specific to the P30 protein of *Mycoplasma pneumoniae*, and produced by a hybridoma deposited with Deposition Number NITE BP-01880 or NITE BP-01881.

15. A labeled antibody comprising the specific monoclonal antibody of claim 14 labeled with a metal colloid particle.

16. The labeled antibody according to claim 15, wherein the metal colloid particle is a gold colloid particle.

17. A hybridoma deposited with Deposition Number NITE BP-01880 or NITE BP-01881.

* * * * *